Figure 1:
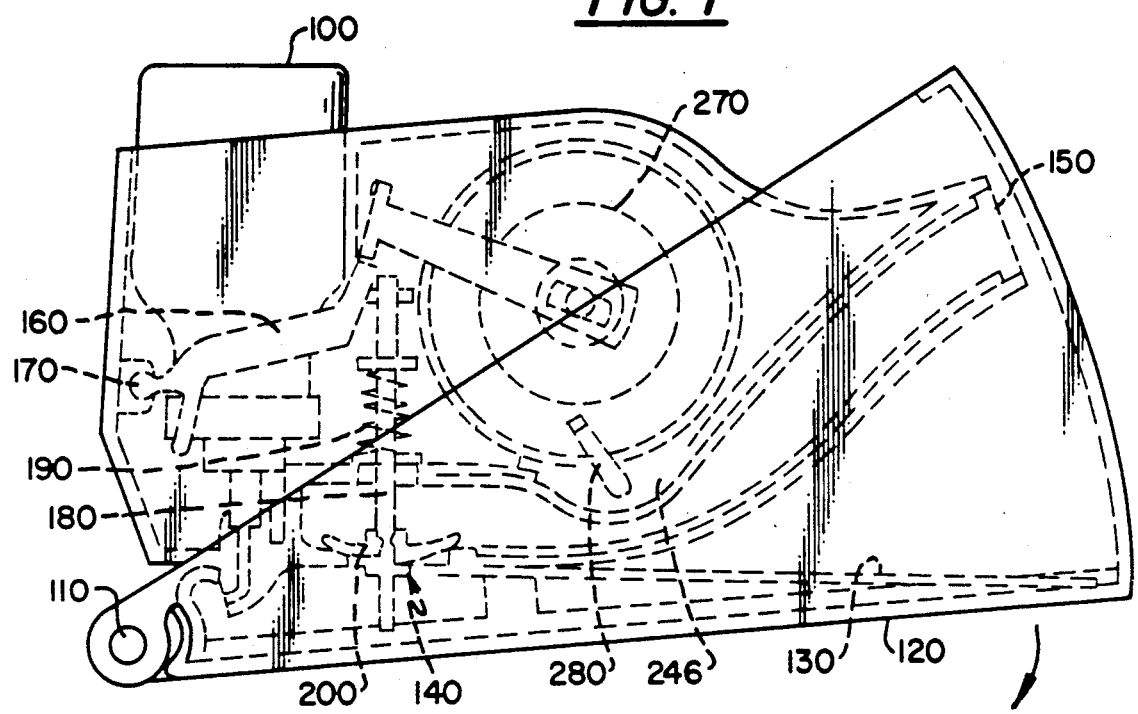

_United States Patent_ [19]

Zoltan et al.

[11] Patent Number: 5,027,806

[45] Date of Patent: Jul. 2, 1991

[54] MEDICATION DELIVERY SYSTEM PHASE TWO

[75] Inventors: Bart J. Zoltan, Old Tappan, N.J.; Beth L. Laube; George K. Adams, III, both of Baltimore, Md.; Clark F. Bow, Newton, N.J.; Ralph J. Devito, Stanhope, N.J.; Walter Harrington, Flanders, N.J.; Louis S. Hoffman, Moristown, N.J.; Charles B. Sanders, Cedar Grove, N.J.

[73] Assignee: The Johns Hopkins University, Baltimore, Md.

[21] Appl. No.: 462,881

[22] Filed: Jan. 3, 1990

Related U.S. Application Data

[63] Continuation of Ser. No. 253,039, Oct. 4, 1988, abandoned.

[51] Int. Cl.$^5$ .................. A61M 11/00; A61M 16/00
[52] U.S. Cl. .......................... 128/200.23; 128/203.28
[58] Field of Search .................. 128/200.14, 200.18, 128/200.23, 200.16, 203.12, 203.13, 203.15, 203.21, 203.25, 204.25, 204.28, 205.21, 205.24, 205.25, 228; 272/99

[56] References Cited

U.S. PATENT DOCUMENTS

| 733,027 | 7/1903 | Goldan | 128/203.28 |
| 1,695,930 | 12/1928 | Schroder | 128/203.28 |
| 3,960,148 | 1/1976 | Dryden | 128/203.28 |
| 4,077,404 | 3/1978 | Elam | 128/206.28 |
| 4,790,305 | 12/1958 | Zoltan et al. | 128/200.23 |

FOREIGN PATENT DOCUMENTS

| 3513628 | 10/1986 | Fed. Rep. of Germany | 128/203.28 |
| 773018 | 8/1934 | France | 128/203.28 |

_Primary Examiner_—Randall L. Green
_Assistant Examiner_—K. M. Reichle
_Attorney, Agent, or Firm_—Cushman, Darby & Cushman

[57] ABSTRACT

Improved, compact apparatus for use in inhaling pharmaceutical aerosols. The apparatus increases aerosol deposition to the bronchiolus while it limits deposition in the oropharynx. The volumetric flow rate is limited by the use of orifices in the far end of the rigid holding chamber. The invention is also designed to make it easy for the patient to inhale the medication at the proper point in his respiratory cycle. Besides the rigid holding chamber the apparatus of the invention utilizes a unique and compact integrated flow meter to deliver to the patient a volume of unmedicated ambient air before the inhalation of the medicine containing aerosol. When the apparatus is not in use, it folds up, so that some of the integrated flow meter apparatus, and the mouthpiece are located inside the rigid holding chamber thereby minimizing the size of the device.

18 Claims, 3 Drawing Sheets

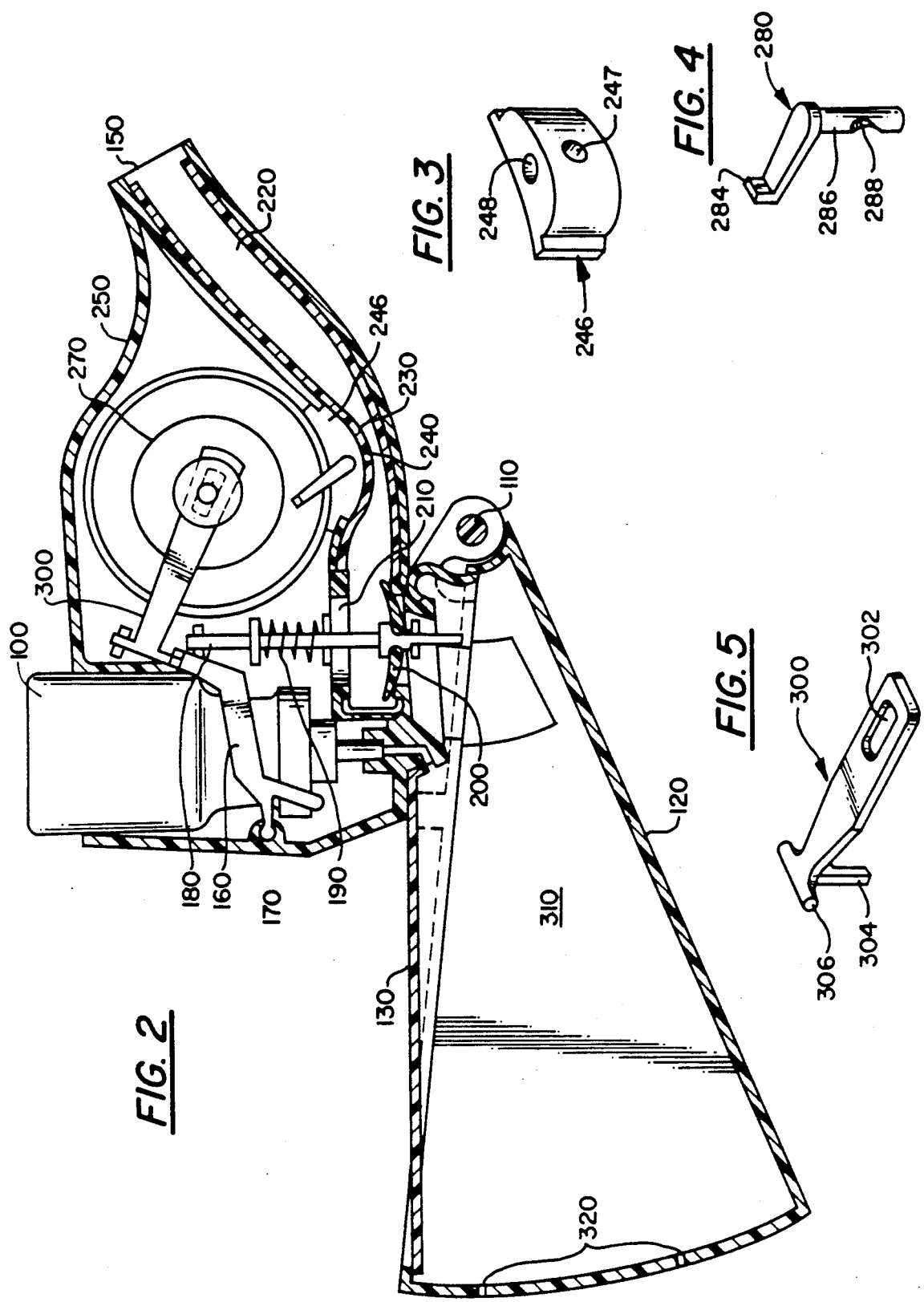

MEDICATION DELIVERY SYSTEM PHASE TWO

This is a continuation of application Ser. No. 07/253,039, filed Oct. 4, 1988, which was abandoned upon the filing hereof.

BACKGROUND OF THE INVENTION

1. Field of the Invention

This invention relates to the administration of pharmaceuticals which are active when delivered to the lung as an aerosol.

Certain medications, especially those intended for the treatment of acute and chronic respiratory disorders, are most effective when inhaled directly into the lungs. Thus, numerous pharmaceutical products are marketed as aerosols administered from metered dose inhalers.

While aerosol therapies have been very successful, there have been a number of difficulties in dispensing the aerosols properly.

A major problem of aerosol therapy is achieving deposition of the aerosol on the walls of small bronchi and bronchioles, where the action of the medication is most often required. Less than ten percent of the medication delivered by standard metered dose inhalers reaches the typical patient's lungs. Most of the ninety percent of the medication which does not penetrate to the target area is deposited in the mouth, throat, and trachea, and is eventually ingested. A small fraction of the aerosol is exhaled. The medication which deposits in the mouth and throat may lead to dysphonia and/or oral and laryngeal candidiasis while the medication which is ingested serves no medical purpose to the patient and is responsible only for undesirable side effects.

Therefore the delivery of same drugs via aerosol has been considered impractical. Nevertheless the aerosol delivery of many drugs, if possible, would present an attractive alternative to the therapies that are currently available. An example of such a substance is polypeptide.

Polypeptides are made up of amino acid sequences, and include large molecules like insulin, and all of the products of recombinant DNA (rDNA) techniques. These molecules are broken down in the digestive tract and, therefore, the intact polypeptide molecule is not absorbed into the bloodstream. Accordingly, the only practical way to administer these drugs is by injection, although the nasal route of administration would be desirable and has been suggested, but has not been practical.

Another example is tissue plasminogen activator (t-PA) which appears to be successful in halting damage done to cardiac muscle during myocardial infarction. There could be an advantage to being able to utilize this drug as an aerosol for inhalation so that it could be administered without the need to wait for a physician or paramedic.

Delivery of therapy in pneumonia directly to the lung would also be desirable. Ordinarily, the concentration of antibiotic in the sputum is only two to three percent of the concentration in blood. However, in pneumonia, antibiotic concentration in the sputum is believed to be the determining factor for efficacy of the therapy. Therefore, direct delivery of the antibiotic may improve the effectiveness of the treatment.

In order to avoid the problems encountered with aerosol delivery, noted above, the aerosol should consist of small particles, less than 5 microns, since larger particles cannot negotiate the sharp turns to the lung and are deposited in the oropharynx due to inertial effects. Particles that persist in the airstream beyond the oropharynx may deposit in the larynx and on the walls of the trachea and large bronchi as a result of turbulence, particularly if the patient inhales at a volumetric flow rate above 30 liters per minute.

Metered dose inhalers deliver aerosol at a very high velocity directly into the patient's mouth, and most of the medication impacts and is deposited in the mouth. This high initial velocity of the aerosol is a major factor in the ineffectiveness of many inhaler systems. In order to minimize mouth deposition it has been determined that the volumetric flow rate of the inhaled aerosol should be below 30 liters per minute.

After the medication has been inhaled it is best to continue inhaling to total lung capacity to promote greater penetration of drug to the lung periphery. One should then hold that breath for four to ten seconds, if possible, to allow for sedimentation of particles onto the airway surface.

Several pharmaceutical manufacturers have included, or sold separately with their aerosol products, what they refer to variously as "spacers", "inhalers", "drug inhalers", "oral adapters", "spacer-inhalers", and "spray inhalers" to be used in conjunction with their products.

Of the related devices known to the inventors, only Sackner et al., U.S. Pat. No. 4,484,577, marketed as the INSPIREASE TM from Key Pharmaceutical, addresses the known problems of aerosol inhalation. The INSPIREASE TM is essentially a collapsible bag into which the medication is metered, and from which the patient inhales. The INSPIREASE TM mouthpiece contains a whistle which is silent at low flow rates but sounds when the patient is inhaling too rapidly.

Further, laboratory equipment has been developed which allows inspired air to be measured using a pneumotachograph. The flow rate signal is integrated by a computer, and an aerosol canister containing the medication is actuated automatically at a predetermined lung volume using a solenoid mounted on top of the aerosol actuator. While this system is suitable for experimental studies, it is impractical for use in routine therapy because of size and cost.

Thus, there is a need for a device to aid patients in taking their aerosol medications. The device should limit the volumetric flow rate of the medication and aerosol as they enter the mouth, and should allow the medication to be inhaled at a predetermined point in the respiratory cycle. It should be possible to inhale to maximum capacity.

The size of the device should allow it to be carried by the patient without too much inconvenience, and the cost to the patient should be low.

SUMMARY OF THE INVENTION

The present invention is a continuation of the developments which are taught in two prior patent applications, Ser. No. 06/877,331, filed June 23, 1986, now U.S. Pat. No. 4,790,308, and a copending application of Zoltan et. al. filed on even date herewith and titled MEDICATION DELIVERY SYSTEM PHASE ONE.

Briefly, the apparatus described in Ser. No. 877,331 delivered a volume of unmedicated air from a collapsible holding chamber to the patient, after which it automatically began to deliver the aerosolized medication.

The volumetric flow rate of the inhaled medication was maintained below the upper limits of volumetric flow rate for optimal dosing. While that design met all of the criteria for a safe and effective design, the method of holding a volume of unmedicated air can be very cumbersome.

In pulmonary physiology, the term vital capacity is the volume of air a patient can voluntarily exhale after having inhaled to total lung capacity. The vital capacity can vary from 2 to 5 liters depending on fitness, disease, gender and age. There is a lack of agreement as to the precise optimum in lung volume at the time of inhalation that will maximize the benefit from inhaled aerosols. In the medical literature, the optimal lung volume that is recommended ranges from 20 percent to 80 percent of vital capacity.

The apparatus described in the copending application entitled MEDICATION DELIVERY SYSTEM PHASE ONE eliminated the cumbersome volume of unmedicated air altogether.

However, the problem of designing a practical, small device, which incorporated all of the features of the original device, but did so in a much smaller package remained. Thus it became necessary to design a device which would meter to the patient an amount of unmedicated air, but the design of which would be very small, yet reliable. Those design criteria have been met by the present embodiment of the invention.

Thus, it is an object of the present invention to overcome some of the disadvantages associated with the prior art, and to provide the patient and his physician with a compact and practical means of taking aerosol medication in an optimal manner at low cost.

This object is achieved by metering the aerosol medication into a rigid holding chamber, from which rigid holding chamber the patient will inhale the medication. The rigid holding chamber is designed in such a way as to allow the patient to inhale to his total lung capacity. Throughout this specification, the term rigid chamber refers to the chamber while in use. Indeed, for the sake of portability, it is desirable to fold or collapse the subject invention in to a small space. Thus, the term rigid is meant to be applied in the same way that an umbrella may be described as rigid when in use, although it can be stored in a closed configuration and extended prior to use.

The volumetric flow rate is limited by the use of orifices in the far end of the rigid holding chamber. The orifices are nominally sized for the typical frail patient, with provisions for closing one or several orifices if the physician or the patient feel that the nominal setting is inappropriate for a specific patient.

Another object of the invention is to make it easy for the patient to inhale the medication at the proper point in his respiratory cycle. Besides the rigid holding chamber the apparatus of the invention utilizes a unique and compact means of metering, essentially an integrated flow meter, to deliver to the patient a volume of unmedicated ambient air before the inhalation of the medicine containing aerosol.

The integrated flow meter feature can be adjusted at the discretion of the physician to set the volume of ambient air to be inhaled by the patient before the medication containing aerosol is to be inhaled. This volume should be adjusted depending on the condition of the patient and on the judgment of the physician.

When the apparatus is not in use, it folds up, so that some of the integrated flow meter apparatus, and the mouthpiece are located inside the rigid holding chamber thereby minimizing the size of the device.

In preparation for use the patient must open up the device by pulling on the inner assembly of the device, thereby causing the integrated flow meter and the mouthpiece to rotate about a first axis of rotation, and exit from the rigid holding chamber, the now two halves must again be rotated to extend the device into its use position. The second rotation is about an axis at a right angle to the first axis of rotation.

In use, the aerosol medication is metered from a standard metered dose inhaler into the rigid holding chamber. The patient then inhales through a mouthpiece. Initially all of the air inhaled is ambient air. When the volume having passed through the integrated flow meter reaches the preset limit, an escapement mechanism closes a valve, thereby closing off the passage of ambient air to the mouthpiece. At this point in the inhalation cycle the patient automatically begins to inhale from the rigid holding volume which contains the aerosolized medication. His volumetric flow rate is limited to 30 liters per minute by the orifices described above. The patient continues to inhale until he reaches his maximum lung capacity, at which time he holds his breach for the time recommended by his physician.

Other objects, features and characteristics of the present invention, as well as the methods of operation and functions of the related elements of the structure, and the combination of parts and economies of manufacture, will become more apparent upon consideration of the following detailed description and the appended claims with reference to the accompanying drawings all of which form a part of this specification, wherein like reference numerals designate corresponding parts in the various figures.

BRIEF DESCRIPTION OF THE DRAWINGS

FIG. 1 shows the complete device in its storage position;

FIG. 2 shows the complete device in its use position;

FIG. 3 shows the venturi valve provided in accordance with the invention;

FIG. 4 shows the venturi valve stem;

FIG. 5 shows the arm;

FIG. 6 shows the pin;

FIG. 7 shows the valve; and

FIG. 8 shows the diaphragm; and

FIG. 9 shows the exterior of the complete device between its storage position and its use position.

DESCRIPTION OF THE PREFERRED EMBODIMENT

The preferred embodiment of the device is shown in its storage and carrying position in FIG. 1. An industry standard metered dose inhaler (MDI) 100 fits into the invention, and is stored and carried in the device. The device is opened into its use position by first rotating the holding chamber 120 about pivot point 110 in a clockwise direction from the position shown in FIG. 1 to the position shown in FIG. 9 so that element 130 defines a cover for holding chamber 120. Because chamber cover 130 cannot rotate above pivot point 110, further rotation of the cover 130 and chamber 120 combination is not possible. After the initial rotation about 110, the metering portion, the mouthpiece and MDI are all rotated about turret feature 140.

The device is shown in its use position in FIG. 2. The patient is instructed to shake the MDI, therefore the whole device, and to depress the MDI 100, thereby metering a predetermined amount of aerosolized medication into the holding chamber 120. The patient is instructed to then inhale through mouthpiece 150, which is an integral part of the metering part of the invention.

When the MDI is depressed, hinge 160 rotates about pivot point 170 and depresses pin 180, and at the same time compresses spring 190. Attached to pin 180 is a valve 200 made of a compliant material such as rubber. The action of depressing the MDI container 100 closes off the aerosol in holding chamber 120 from reaching the mouthpiece because valve 200 makes an effective and complete seal.

Thus when the patient inhales through mouthpiece 150, the air reaching him is ambient air which can readily make its way through opening 210. The air reaching the patient's mouth travels through a uniquely shaped airpath. Specifically, there is a narrowing of the flowpath, a venturi of air at venturi 230 is less than the area elsewhere. Using Bernoulli's equation, it is clear that at the throat of the venturi the air velocity is increased, and therefore the air pressure is significantly decreased.

A small adjustable opening 240, housed in a venturi valve 246 is located at the throat of the venturi in the airpath. This opening is pneumatically connected to a chamber defined by the back, flat part of housing 250, and which can be adjusted by compliant diaphragm 270.

FIG. 3 shows the venturi valve 246, which contains two mutually perpendicular through holes 247 and 248, which meet one another inside the venturi valve. Hole 247 faces the venturi in the airflow to the patient's mouth, and hole 248 faces the enclosed volume defined by the back of structure 260 and by diaphragm 270.

FIG. 4 shows the venturi valve stem 280, which contains a handle part 282 having a protruding feature 284 to facilitate rotation about an axis defined by cylindrical rod 286. Rod 286 of the venturi valve stem fits snugly into hole 248 in the venturi valve. The venturi valve stem also has a recess 288, which is essentially a segment of a cylinder removed from rod 286, in a direction perpendicular to the longitudinal axis of rod 286.

Figure 9:
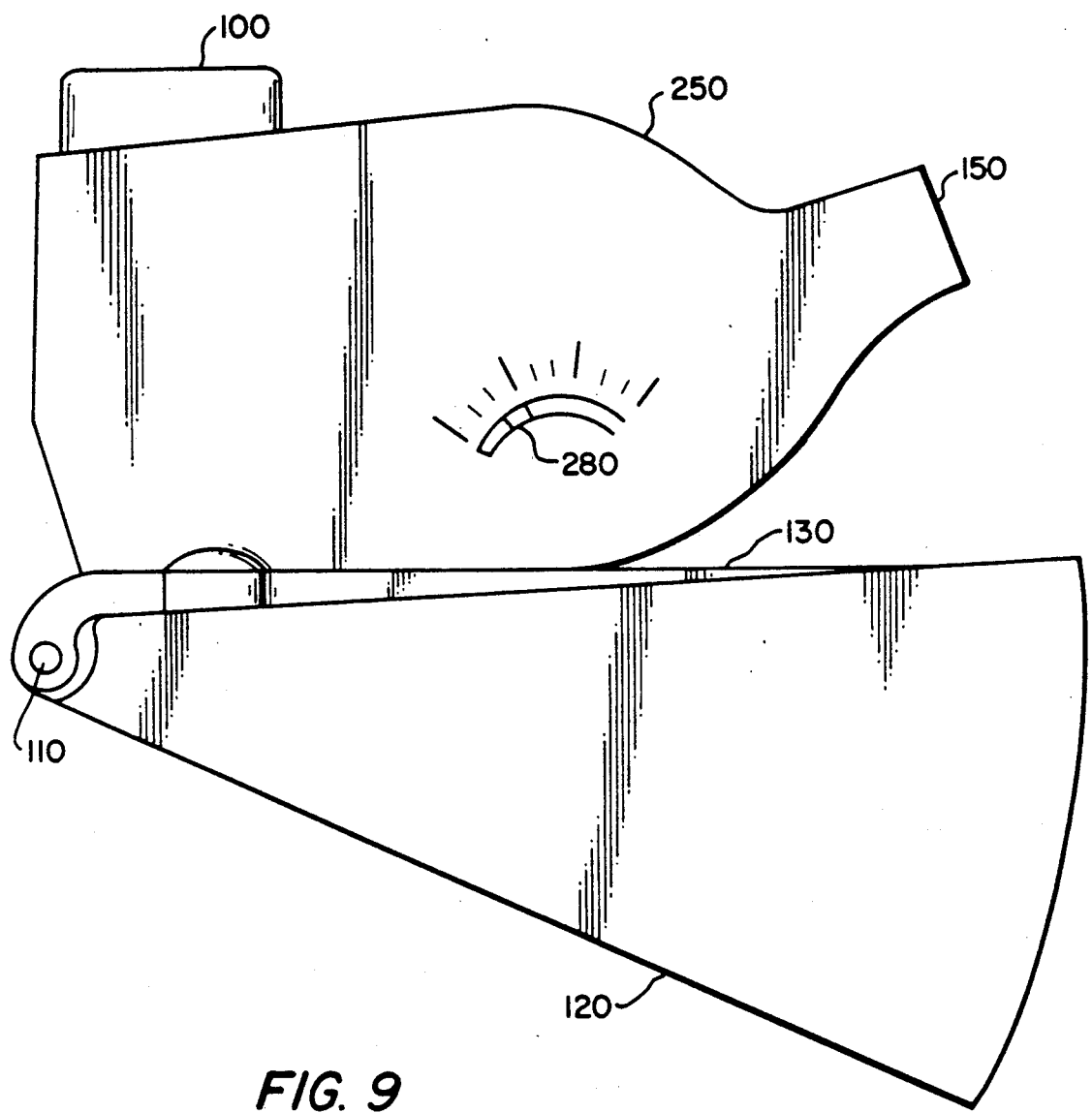

Thus, by rotating the venturi valve stem 280, the area of lower pressure presented to the diaphragm 270 can be adjusted. As is readily apparent to the ordinary artisan, a slot-like aperture can be provided, for example, in the wall of the device for the valve stem 280, as shown in FIG. 9. Furthermore, indicia may be provided, such as along the slot through which the valve stem extends, for indicating the area of lower pressure presented to diaphragm 270.

In use, when the patient is inhaling ambient air, he is also slowly drawing air from the volume defined by the diaphragm 270. The rate at which this volume is depleted is dependent upon the position of venturi valve stem 280.

Lever arm 300 can be seen in FIG. 2 as being attached at one end to the center of diaphragm 270, and as acting on pin 180.

FIG. 5 shows the lever arm 300 in greater detail. The lever arm contains an elongated slot 302, which is for attachment to the center of the diaphragm. It also has protuberances 304, and 306, for engagement with pin 180.

Figure 6:
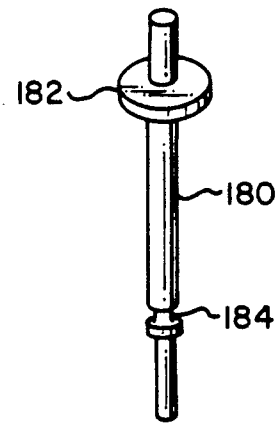
Figure 7:
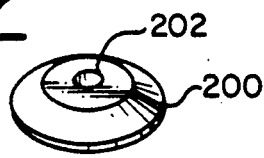

FIG. 6 is a detail of pin 180. It contains a narrow cylindrical flange 182 for engagement with lever 300, and groove 184 for attachment of valve 200. Valve 200 is shown in detail in FIG. 7 and, as can be seen, has an aperture 202 for receiving pin 180.

Figure 8:
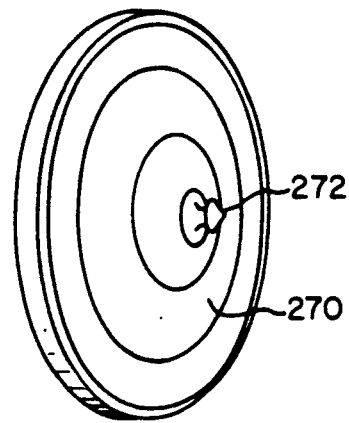

FIG. 8 shows the diaphragm 270, with feature 272 for attachment to arm 300 through opening 302.

In use, after the MDI 100 has been depressed, valve 200 seats and closes off the volume containing the medication. Lever 300 rests on pin 180 and keeps the valve in the closed position. As the patient inhales, diaphragm 270 begins to collapse upon the volume of air it had contained. When the diaphragm has collapsed to a predetermined point, lever 300 disengages from pin 180, and the valve is moved into its second stable position by the force of spring 190.

At this time the patient can only inhale air from chamber 310 the air which contains the aerosolized medication. Holding chamber 120 contains flow rate limiting orifices 320 at its far end. The purpose of orifices is to limit the rate of inhalation of the aerosolized medication to below 30 liters per minute. In the preferred embodiment nine orifices of 0.026" diameter were provided. The orifices are such that they can readily be blocked, one by one, by any suitable means if deemed necessary to customize the level of resistance to the needs of the patient.

While the invention has been described in connection with what is presently considered to be the most practical and preferred embodiment, it is to be understood that the invention is not limited to the disclosed embodiment, but, on the contrary, is intended to cover various modifications and equivalent arrangements included within the spirit and scope of the appended claims.

We claim:

1. A device for administering a medication to a patient comprising:

means for receiving a medication container;

a rigid housing for holding medication, said rigid housing having a first end, a second end, and a main body portion so as to define a chamber therewithin, said first end having an aperture defined therethrough, and said second end having at least one orifice for limiting the volumetric rate of flow through said chamber from said second end to said first end;

first conduit means fluidly coupled to said means for receiving and fluidly coupled to said chamber so as to define a flow path for medication therebetween;

a mouthpiece;

second conduit means fluidly coupled to said mouthpiece and to said aperture so as to define a flow path therebetween;

means defining a variable volume chamber for unmedicated ambient air;

third conduit means fluidly coupled to said variable volume chamber and to said second conduit means so as to define a flow path therebetween; and means for initially allowing unmedicated, ambient air to flow from said variable volume chamber through said third conduit means and said second conduit means to said mouthpiece and, after a predetermined amount of unmedicated ambient air has flowed from said variable volume chamber to said mouthpiece, for allowing medicated air to flow from said chamber in said rigid housing through said second conduit means to said mouthpiece, said means for initially allowing including valve means for closing said aperture when medication is conveyed from said means for receiving to said chamber in said rigid housing and for opening said aperture when said variable volume chamber has decreased in volume by a predetermined amount;

whereby a patient can inhale a volume of unmedicated ambient air through said mouthpiece and thereafter automatically inhale medication from said chamber at a flow rate limited by said at least one orifice.

2. A device as in claim 1, in combination with a medication container, said medication container including a pressurized aerosol.

3. A device as in claim 2, wherein the medication container includes a spray dispenser means.

4. A device as in claim 1, wherein said at least one orifice is sized to limit the volumetric flow of air through said rigid housing under the influence of typical inhalation force to 30 liters per minute or less.

5. A device as in claim 4, wherein there are at least two orifices and wherein at least one of said orifices may be closed off.

6. A device as in claim 1, further comprising means for varying the volumetric flow through said third conduit means.

7. A device as in claim 6, further including indicia means for indicating said volumetric flow through said third conduit means.

8. A device as in claim 1, further comprising a venturi defined along a portion of said second conduit means, said third conduit means being fluidly coupled to said second conduit means at a throat of said venturi and wherein said means defining a variable volume chamber comprises a flexible diaphragm element coupled to a rigid wall element so as to define a collapsible chamber.

9. A device as in claim 8, wherein said means for initially allowing includes lever arm means operatively coupled to said flexible diaphragm element for holding said valve means in tis closing position until said collapsible chamber has collapsed a predetermined amount.

10. A device for administering a medication to a patient comprising:

means for receiving a medication container;

a rigid housing for holding medication, said rigid housing having a first end, a second end, and a main body portion so as to define a chamber therewithin, said first end having an aperture defined therethrough, and said second end having at least one orifice for limiting the volumetric rate of flow through said chamber from said second end to said first end;

first conduit means fluidly coupled to said means for receiving and fluidly coupled to said chamber so as to define a flow path for medication therebetween;

a mouthpiece;

second conduit means fluidly coupled to said mouthpiece and to said aperture so as to define a flow path therebetween;

means defining a variable volume chamber for unmedicated ambient air and including a flexible diaphragm element coupled to a rigid wall element so as to define a collapsible chamber;

third conduit means fluidly coupled to said variable volume chamber and to said second conduit means so as to define a flow path therebetween;

a venturi defined in said second conduit means and extending along a portion of the length thereof, said third conduit means being fluidly coupled to said second conduit means at a throat of said venturi; and means for initially allowing unmedicated, ambient air to flow from said variable volume chamber through said third conduit means and said second conduit means to said mouthpiece and, after a predetermined amount of unmedicated ambient air has flowed from said variable volume chamber to said mouthpiece, for allowing medicated air to flow from said chamber in said rigid housing through said second conduit means to said mouthpiece;

whereby a patient can inhale a volume of unmedicated ambient air through said mouthpiece and thereafter automatically inhale medication from said chamber at a flow rate limited by said least one orifice.

11. A device as in claim 10, in combination with a medication container, said medication container including a pressurized aerosol.

12. A device as in claim 11, wherein the medication container includes a spray dispenser means.

13. A device as in claim 10, wherein said at least one orifice limits the volumetric flow of air through said rigid housing to 30 liters per minute or less.

14. A device as in claim 13, wherein there are at least two orifices and wherein at least one of said orifices may be closed off for the purpose of limiting the flow of air.

15. A device as in claim 10, further comprising means for varying the volumetric flow through said third conduit means.

16. A device as in claim 15, further including indicia means for indicating said volumetric flow through said third conduit means.

17. A device as in claim 10, wherein said means for initially allowing includes valve means for closing said aperture when medication is conveyed from said means for receiving to said chamber in said rigid housing and for opening said aperture when said collapsible chamber has collapsed a predetermined amount.

18. A device as in claim 17, wherein said means for initially allowing includes lever arm means operatively coupled to said flexible diaphragm element for holding said valve means in its closing position until said collapsible chamber has collapsed a predetermined amount.

* * * * *